United States Patent
Musso et al.

(10) Patent No.: US 9,936,694 B2
(45) Date of Patent: Apr. 10, 2018

(54) COMPOSITIONS AND METHODS FOR ATTRACTING AND STIMULATING FEEDING BY MICE AND RATS

(71) Applicant: SCOTTS CANADA, LTD, Toronto (CA)

(72) Inventors: Antonia E. Musso, Burnaby (CA); Stephen J. Takacs, Burnaby (CA); Regine M. Gries, Coquitlam (CA); Gerhard J. Gries, Coquitlam (CA)

(73) Assignee: Scotts Canada Ltd., Toronto, Ontario (CA)

( * ) Notice: Subject to any disclaimer, the term of this patent is extended or adjusted under 35 U.S.C. 154(b) by 0 days.

(21) Appl. No.: 14/892,662

(22) PCT Filed: May 7, 2014

(86) PCT No.: PCT/CA2014/050435
§ 371 (c)(1),
(2) Date: Nov. 20, 2015

(87) PCT Pub. No.: WO2014/186885
PCT Pub. Date: Nov. 27, 2014

(65) Prior Publication Data
US 2016/0100575 A1    Apr. 14, 2016

Related U.S. Application Data

(60) Provisional application No. 61/826,432, filed on May 22, 2013.

(51) Int. Cl.
| | | |
|---|---|---|
| A01N 25/00 | (2006.01) | |
| A01N 25/10 | (2006.01) | |
| A01K 97/04 | (2006.01) | |
| A01K 29/00 | (2006.01) | |
| A01N 35/06 | (2006.01) | |
| A01N 31/02 | (2006.01) | |
| A01N 35/02 | (2006.01) | |
| A01N 37/02 | (2006.01) | |
| A01N 43/16 | (2006.01) | |
| A23K 10/30 | (2016.01) | |
| A23K 10/37 | (2016.01) | |
| A23K 20/105 | (2016.01) | |
| A23K 20/126 | (2016.01) | |
| A23K 20/158 | (2016.01) | |
| A23K 20/163 | (2016.01) | |
| A23K 20/10 | (2016.01) | |
| A23K 50/50 | (2016.01) | |

(52) U.S. Cl.
CPC ........... *A01N 35/06* (2013.01); *A01N 25/004* (2013.01); *A01N 31/02* (2013.01); *A01N 35/02* (2013.01); *A01N 37/02* (2013.01); *A01N 43/16* (2013.01); *A23K 10/30* (2016.05); *A23K 10/37* (2016.05); *A23K 20/10* (2016.05); *A23K 20/105* (2016.05); *A23K 20/126* (2016.05); *A23K 20/158* (2016.05); *A23K 20/163* (2016.05); *A23K 50/50* (2016.05); *Y02P 60/877* (2015.11)

(58) Field of Classification Search
None
See application file for complete search history.

(56) References Cited

U.S. PATENT DOCUMENTS

2006/0263488 A1* 11/2006 Pupko ............... A21D 13/0038
426/94

FOREIGN PATENT DOCUMENTS

| WO | WO 96/003037 | * | 2/1996 | ............. A01N 25/00 |
| WO | WO 2013/003946 | * | 1/2013 | ............. A01N 43/08 |

OTHER PUBLICATIONS http://web.archive.org/web/20120118025825/http://www.alaskaproteinrecovery.com/salmonoil; website titled Alaska Protein Recovery; accessed Aug. 4, 2016; web archive version dated Jan. 18, 2013 downloaded; 2-pg pdf.*

* cited by examiner

*Primary Examiner* — Jeffrey T. Palenik
(74) *Attorney, Agent, or Firm* — Ulmer & Berne LLP

(57) ABSTRACT

This invention describes novel food bait compositions that can be used alone or in combination with blends of attractive compounds to induce attraction and feeding by mice and rats. Said compositions and blends can be used to induce mice and rats to be captured in traps or to approach and remain in a location where they will be exposed to a rodenticide.

21 Claims, 10 Drawing Sheets

COMPOSITIONS AND METHODS FOR ATTRACTING AND STIMULATING FEEDING BY MICE AND RATS

CROSS-REFERENCE TO RELATED APPLICATIONS

This application is a National Stage Application under 35 U.S.C. § 371 of PCT International Application No. PCT/CA14/50435 filed May 7, 2014, and claims the priority benefit of U.S. Provisional Patent App. No. 61/826,432 filed May 22, 2013.

FIELD OF THE INVENTION

This invention relates to compositions and methods for attracting and stimulating feeding by mice and rats.

BACKGROUND OF THE INVENTION

Takács et al. (2013), incorporated by reference herein in its entirety, teach that a blend of synthetic chemicals in combination with dry-rendered lard and cracklings provides an effective trap bait, for both mice and rats. A composition primarily comprising a core group of six attractive semiochemicals (2-hydroxy-3-methylcyclopent-2-en-1-one, butyric acid, 2,3-butadione, 3-methylbutanal, 5-methyl-(E)-2-hepten-4-one and γ-octalactone) provides a basis for attraction, and the lard and cracklings provide a feeding stimulant. Other semiochemicals that could be combined with lard and cracklings included: 4-hydroxy-2,5-dimethyl-furan-3-one, 5-methyl-4-heptanone, nonanoic acid, decanoic (capric) acid, dodecanoic (lauric) acid, tetradecanoic (myristic) acid, hexadecanoic (palmitic) acid, (Z)-octadec-9-enoic (oleic) acid, octadecanoic (stearic) acid, lactic acid and glycerol.

All testing by Takács et al. (2013) was done with female house mice, *Mus musculus*, and Norway rats, *Rattus norveigicus*. The attractive six-component semiochemical blend was given the trivial name Entice. It was equally effective against both sexes of both species. However, when the current inventors compared the response of house mice and Norway rats to Entice with lard and cracklings or to Provoke® Mouse Attractant or Provoke® Rat Attractant (Bell Laboratories, Inc., Madison, Wis., USA), respectively, female rats unexpectedly fed preferentially on Provoke. Thus the above composition may not have performed optimally as a commercial product used in certain operational settings. Improved compositions and methods equally effective against both sexes of both rodent species, and other rodent species, are desirable.

SUMMARY OF THE INVENTION

This invention relates to compositions and methods for attracting and stimulating feeding by mice and rats. According to one aspect, the composition comprises a cereal flour, a cereal bran, a gelling agent, a sugar, an oil, an emulsifier and a humectant.

According to some embodiments, the cereal flour may be oat flour, rice flour, wheat flour, spelt flour, barley flour, rye flour, soybean flour, and/or corn flour. According to an example embodiment, the cereal flour is a mixture of oat flour and rice flour. In such embodiments, the composition may comprise oat flour at 10-20% by weight, and rice flour at 5.0-15% by weight.

According to some embodiments, the cereal bran may be oat bran, rice bran, wheat bran, spelt bran, barley bran, rye bran, soybean bran, and/or corn bran. According to an example embodiment, the cereal bran is wheat bran flour. In some embodiments, the composition may comprise the cereal bran at 1.0-10% by weight.

According to some embodiments, the gelling agent may be agar, gelatin, pectin, guar, carob, locust bean, starch and/or modified starches. According to an example embodiment, the gelling agent is gelatin or agar. In some embodiments, the composition may comprise the gelling agent at 0.1 to 5.0% by weight.

According to some embodiments, the sugar may be a monosaccharide (e.g. fructose, glucose, galactose, xylose, ribose) or a disaccharide (e.g. sucrose, lactose, maltose). According to an example embodiment, the sugar is fructose. In some embodiments, the composition may comprise the sugar at 0.1-5.0% by weight.

According to some embodiments, the oil may be a vegetable oil (e.g. safflower oil, soybean oil, cottonseed oil, canola oil, sunflower oil, hempseed oil, olive oil, rapeseed oil, corn oil) or a fish oil (e.g. salmon oil, cod liver oil, herring oil, sardine oil, mackerel oil). According to an example embodiment, the oil is a fish oil, in particular salmon oil. In some embodiments, the composition may comprise the oil at 0.01 to 1.0% by weight.

According to some embodiments, the emulsifier may be a lecithin, monoglyceride, diglyceride, monostearate, polystearate, and/or propylene glycol ester. According to an example embodiment, the emulsifier is soy lecithin. In some embodiments, the composition may comprise the emulsifier at 0.01 to 1.0% by weight.

According to some embodiments, the humectant may be carrageenan gum, carboxymethyl cellulose, polyacrylic acid and/or xanthan gum According to an example embodiment, the humectant is carrageenan gum powder.

According to some embodiments, the composition may also comprise one or more compounds emitted by recently deceased animals, i.e. a necromone. According to an example embodiment the necromone is dimethyltrisulfide.

According to some embodiments, the composition may include one or more of the following seven volatile attractive semiochemicals, namely 2-hydroxy-3-methylcyclopent-2-en-1-one, butyric acid, 2,3-butadione, 3-methylbutanal, 5-methyl-(E)-2-hepten-4-one, 5-methyl-4-heptanone and γ-octalactone.

According to some embodiments, the method of attracting and inducing feeding by mice and rats includes the steps of heat treating the composition and placing the heat treated composition in or near traps for capturing mice or rats. Heat treating the composition may be accomplished by mixing one or more components of the composition (e.g. the gelling agent, preservative and/or the humectant) with boiling hot water and then combining with the remaining components. In some embodiments the heat treated composition may be combined with a rodenticide.

According to some embodiments, the targeted mouse species may be *Mus musculus*.

According to some embodiments, the targeted rat species may be *Rattus norvegicus, Rattus rattus, Rattus annandalei, Rattus enganus, Rattus everetti, Rattus exulans, Rattus hainaldi, Rattus hoogerwerfi, Rattus korinchi, Rattus macleari, Rattus montanus, Rattus morotaiensis, Rattus nativitatis, Rattus ranjiniae, Rattus sanila, Rattus stoicus, Rattus timorensis, Rattus nitidus, Rattus pyctoris, Rattus turkestanicus, Rattus adustus, Rattus andamanensis, Rattus argentiventer, Rattus baluensis, Rattus blangorum, Rattus burrus, Rattus*

*hoffmanni, Rattus koopmani, Rattus losea, Rattus lugens, Rattus mindorensis, Rattus mollicomulus, Rattus osgoodi, Rattus palmarum, Rattus rattus, Rattus satarae, Rattus simalurensis, Rattus tanezumi, Rattus tawitawiensis, Rattus tiomanicus, Rattus bontanus, Rattus foramineus, Rattus marmosurus, Rattus pelurus, Rattus salocco, Rattus xanthurus, Rattus arfakiensis, Rattus arrogans, Rattus elaphinus, Rattus feliceus, Rattus giluwensis, Rattus jobiensis, Rattus leucopus, Rattus mordax, Rattus niobe, Rattus novaeguineae, Rattus omichlodes, Rattus pococki, Rattus praetor, Rattus richardsoni, Rattus steini, Rattus vandeuseni, Rattus verecundus, Rattus colletti, Rattus fuscipes, Rattus lutreolus, Rattus sordidus, Rattus tunneyi,* or *Rattus villosissimus*. According to an example embodiment, the targeted rat species is *Rattus norvegicus*.

DESCRIPTION OF THE DRAWINGS

In drawings which show non-limiting embodiments of the invention.

DETAILED DESCRIPTION

Figure 1:
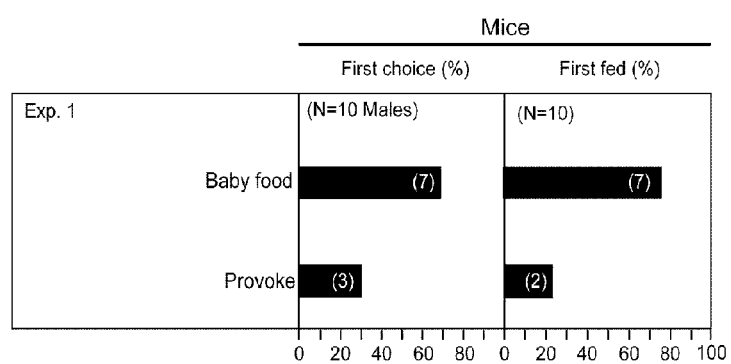
FIG. 1 illustrates: (a) the percent of male house mice, *Mus musculus*, in Experiment 1 entering first in a T-tube bioassay apparatus (see FIG. 1 in Takács et al. 2013) the aquarium baited with the cereal-based baby food (Heinz Mixed Cereal baby food) or the aquarium baited with the control bait (Provoke® Mouse Attractant), and (b) the percentage of mice that fed first on the cereal-based baby food.

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

The invention can be further understood by reference to the following examples, which are provided by way of illustration and are not meant to be limiting. Unless otherwise noted in the following examples, rats are Norway rats and mice are house mice.

Example #1

Screening for Feeding Stimulants

Captures of mice and rats in snap traps rely on stimulation of feeding by the target rodent. If the feeding response retains the animal long enough in the right position the snapping mechanism will be triggered and the rodent will be captured and killed. Thus, effective feeding stimulants are an essential component of a rodent bait. Many substances have been used as trap baits, but scientific research done to select the most preferred baits is lacking. To test the feeding response of mice and rats to potential alternatives to lard and cracklings, many experiments were run, with two, three or four food choices each, and 5-10 animals per experiment. The present inventors tested the following 30 foodstuffs: 1) oat: Rogers Porridge Oats, 1.35 kg, Rogers Food Ltd., Armstrong, BC, Canada; 2) wheat: collected from fields in southern Saskatchewan, Canada; 3) barley: Golden Chef Pot Barley (Orge Mondee), Golden Boy Foods Ltd., Burnaby, BC, Canada; 4) rice: Uncle Ben's Rice, Boil-in-bag, Effem Inc., Bolton, ON, Canada; 5) wheat bran: Rogers 100% Natural Wheat Bran, Rogers Food, Inc., Armstrong, BC, Canada; 6) lard: obtained from Duna Delicatessen, Vancouver, BC, Canada; 7) Tenderflake: Tenderflake Pure Lard, Maple Leaf Consumer Foods, Mississauga, ON, Canada; 8) sunflower oil: Safflo Sunflower Oil, Unico, Concord, ON, Canada; 9) peanut oil: Planters, JVF Canada, Inc., Toronto, ON, Canada; 10) pea: Green Split Peas, Golden Boy Foods, Ltd., Burnaby, BC, Canada; 11) corn starch: Canada Corn Starch, ACH Food Companies, Inc., Memphis, Tenn., USA; 12) lentil: Red Split Lentils, Golden Boy Foods, Ltd., Burnaby, BC, Canada; 13) beans: Small White Beans, Golden Boy Foods, Ltd., Burnaby, BC, Canada; 14) baby food, Heinz mixed cereal without milk, Heinz Canada, North York, ON, Canada; 15) honey oat cereal: Post Honey Bunches of Oats, Post Foods Canada Corp., Niagara Falls, ON, Canada; 16) "Rat Chow": Lab Diet 5001, Rodent Diet, PMI Nutrition International, LLC, Brentwood, Mo., USA; 17) apple seeds: from apples purchased at Nesters Market, Vancouver, BC, Canada; 18) vanilla pudding: Snack Pack Vanilla, ConAgra Foods Canada, Missisauga, ON, Canada; 19) banana: purchased at Nesters Market, Vancouver, BC, Canada; 20) custard: Ambrosia Devon Custard, Premier Food Group, Long Sutton, Spalding, Lincolnshire, UK; 21) apple sauce: Western Family Applesauce, Overwaitea Food Group LP, Vancouver, BC, Canada; 22) sweet potato: purchased at Nesters Market, Vancouver, BC, Canada; 23) dried soup: Knorr Vegetable Soup Mix, Unilever Canada, Toronto, ON, Canada; 24) gravy: Knorr Classic Roast Gravy Mix Brown, Unilever Canada, Toronto, ON, Canada; 25) oatmeal cookies: Dad's Cookies Oatmeal, Kraft Canada Ltd., Scarborough, ON, Canada; 26) fish food: Nutrafin Basix Staple Food, Rolf C. Hagen, Inc., Montreal, QC, Canada; 27) artichoke: purchased at Nesters Market, Vancouver, BC, Canada; 28) macaroni and cheese: No Name Macaroni and Cheese Dinner, Loblaw Foods, Inc., Brampton, ON, Canada; 29) potato flour: Rob's Red Mill Potato Flour, Rob's Red Mill Natural Foods, Milwaukie, Oreg., USA; 30) molasses: Crosby Family Molasses, Crosby Molasses Company, Ltd., Saint John, NB, Canada. Each food type was weighed, placed on a Petri dish (50×9 mm) and transferred onto a corner of an aquarium (30×30×60 cm), in the centre of which a single mouse or rat was released. After two hours, or until all of one bait had been consumed, the animal was removed, all Petri dishes were retrieved, and the remaining food on each dish was weighed. For each replicate the percentage of each food type eaten was scored.

Of the 30 food sources tested as potential feeding stimulants for mice and rats, a dry cereal-based baby food (Heinz Mixed Cereal without milk), mixed with cold water to a semi-firm mush (hereafter referred to as baby food), was unexpectedly fed on in preference to most other foodstuffs by both mice and rats.

Baby food was then taken as a possible starting point for developing a blend of constituents that could potentially form the basis of an operational food bait for both mice and rats.

Example #2

Comparative Effect of Baby Food and Provoke® Mouse Attractant to Attract and Induce Feeding by Mice Experiment 1 compared the ability of baby food and Provoke® Mouse Attractant (the leading commercial bait) to attract male mice and to induce their feeding. In this experiment, the inventors used the two-choice T-tube bioassay apparatus described by Takács et al. (2013). The apparatus consisted of three glass aquaria (30×30×60 cm) interconnected by a T-tube (75×50 cm, 10 cm diameter). For each replicate, a single mouse was deprived of food (but not water) for 4-6 h, and then placed into Aquarium 1. It was then allowed to enter the stem of the T-tube, walk down it, and when it reached the T-junction make a choice whether to turn left or right and walk down the tube toward the stimulus randomly assigned to and held in Aquarium 2 or Aquarium 3. For each mouse, the inventors scored the aquarium (2 or 3) it entered first, the time it spent in each aquarium and the foodstuff it fed on first. The proportion of time spent in each aquarium was calculated by recording the mouse position every 15 sec; the number of positions in aquaria was then divided by the total bioassay time.

In Experiment 1, 7 of 10 mice entered first the aquarium with baby food and fed on baby food first (FIG. 1).

These results indicated that a cereal-based baby food was potentially a good feeding stimulant to substitute for dry-rendered lard and cracklings, and to be incorporated into a rodent bait.

Example #3

Selection of Ingredients of a Cereal-Based Baby Food as Feeding Stimulants

The present inventors prepared a novel composition based on some of the ingredients of commercial baby food, and gave the composition the name Feedstims #1 for testing. It had the following proportions of constituents by weight: gelatin (1.13%), calcium propionate (0.30%), water (71.2%), oat flour (14.2%), rice flour (8.0%), wheat bran (4.3%), fructose (1.4%), soy lecithin (0.3%) and safflower oil (0.14%). Gelatin and calcium propionate were added to boiling water until dissolved (wet ingredients). Oat flour, rice flour, wheat bran, fructose and soy lecithin (dry ingredients) were combined and blended together with the boiling hot wet ingredients, effectively cooking the dry ingredients. Safflower oil was added and the water/gelatin/calcium propionate solution was poured in. The constituents were mixed together and allowed to cool.

In Experiment 2, the response of mice to Feedstims #1 was compared with that to baby food and to Provoke® Mouse Attractant, using the bioassay apparatus described in EXAMPLE 2. In Experiment 3, female rats were offered a choice between Feedstims #1 and Provoke® Rat Attractant in a large circular galvanized steel bioassay arena (180 cm diameter×60 cm tall). Test stimuli were placed on separate Petri dishes, weighed, and positioned in opposite quadrants of the arena, 10 cm apart from the wall. For each replicate, the test animal was deprived of food, but not water, for 12-14 h, transferred in a bowl (15 cm diameter) to the arena, and released in the arena equidistant from each of the two test stimuli. After 30 min, the animal was removed, and the test stimuli were weighed to determine the percentage of each food stimulus that had been consumed.

Figure 2:
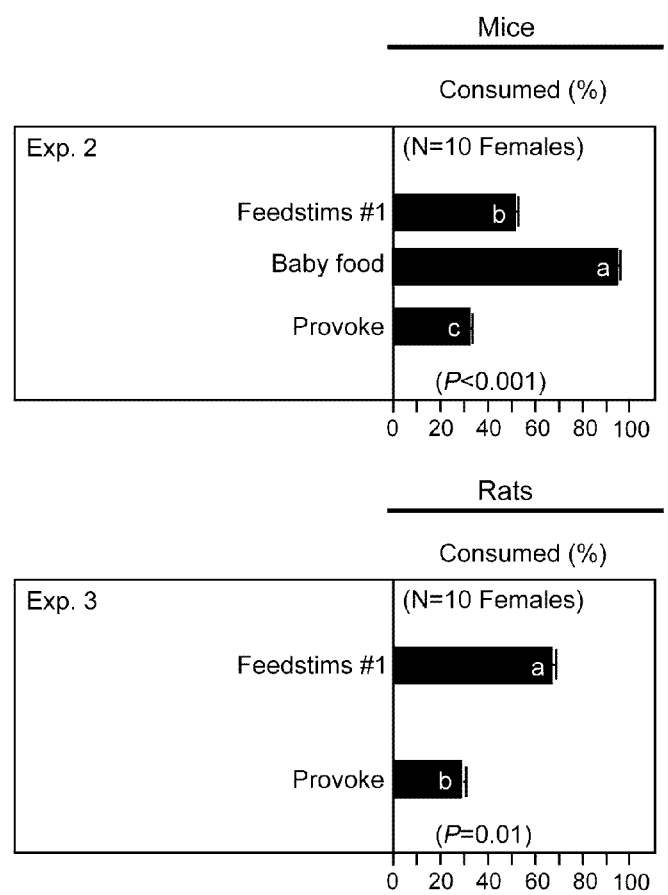
FIG. 2 illustrates the mean percentages (±SE) of each of three food baits eaten by female house mice, *Mus musculus*, in Experiment 2, and the percent of each of two food baits eaten by Norway rats, *Rattus norvegicus*, in Experiment 3. In each replicate of Experiments 2 and 3, food baits were randomly assigned to a corner of an aquarium (60×20×30 cm). Percent consumed data in Experiment 2 were analyzed by ANOVA followed by Student-Newman-Keuls test for multiple comparisons, and in Experiment 3 by Student's t test. In each experiment, bars with different letter superscripts are significantly different (P<0.05).
Figure 3:
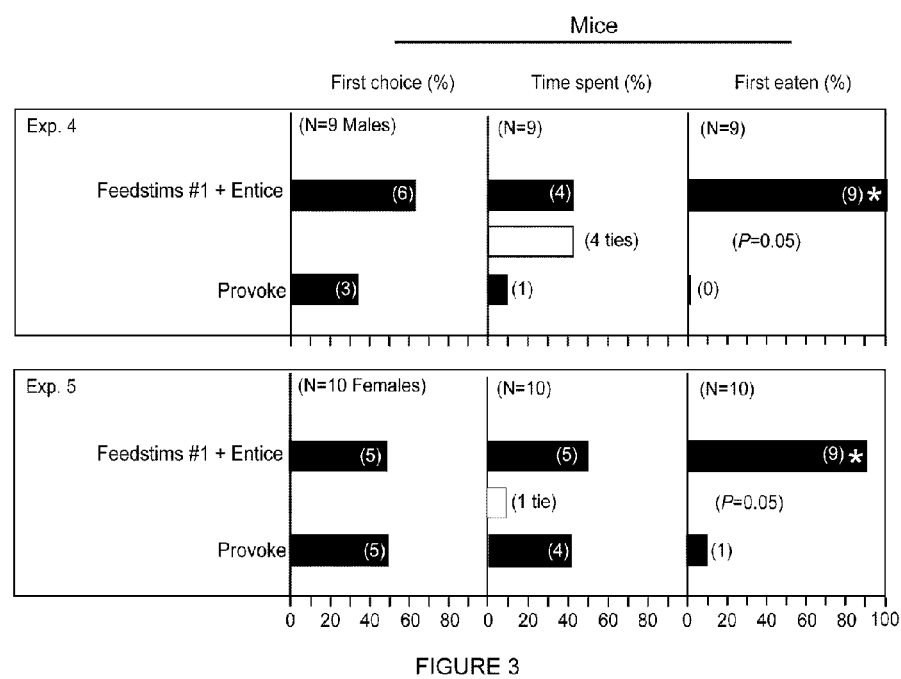
FIG. 3 illustrates: (a) the percent of male and female house mice, *Mus musculus*, in Experiments 4 and 5 entering in a T-tube bioassay apparatus first the aquarium baited with Feedstims #1 (gelatin, water, oat flour, rice flour, wheat bran, fructose, soy lecithin, safflower oil) plus Entice (2-hydroxy-3-methylcyclopent-2-en-1-one; butyric acid; 2,3-butadione; 3-methylbutanal; 6-methyl-(E)-2-hepten-4-one; and γ-octalactone) or the aquarium baited with a control bait (Provoke® Mouse Attractant), (b) the percent time mice spent in each aquarium, and (c) the percent of mice that fed first on the treatment bait or control bait. Data in each set of paired black bars were analyzed by Chi-square tests with Yates' correction for continuity. In each of the six sets of paired bars, bars with an asterisk (*) indicate a significant preference (P<0.05) for the treatment bait.

In Experiment 2, female mice consumed significantly more baby food than Feedstims #1, and significantly more Feedstims #1 than Provoke® Mouse Attractant (FIG. 2). In Experiment 3, female rats consumed significantly more feeding Feedstims #1 than Provoke® Rat Attractant (FIG. 3).

These results clearly and surprisingly indicate that Feedstims #1 is an effective substitute for dry-rendered lard and cracklings as a feeding stimulant for rats. While the commercial baby food was preferred over Feedstims #1 by mice, the preference for Feedstims #1 over Provoke® Mouse Attractant also unexpectedly indicates that Feedstims #1 is an effective substitute for dry-rendered lard and cracklings as a feeding stimulant for mice according to some embodiments.

Example #4

Effect of Adding Entice to Feedstims #1

Female mice in Experiment 2 showed a significant preference for Feedstims #1 over Provoke® Mouse Attractant (FIG. 2), but it was not known if this preference would be enhanced by addition of Entice. Entice semiochemicals represent a mixture of six characteristic odorants from three food types (2-hydroxy-3-methylcyclopent-2-en-1-one from candy; butyric acid, 2,3-butadione, 3-methylbutanal from Swiss cheese; and 6-methyl-(E)-2-hepten-4-one and γ-octalactone from hazelnut) which the inventors have previously shown to attract mice and rats (Takács et al. 2013). A seventh food volatile, 5-methyl-4-heptanone was also shown to be an attractive alternative to butyric acid in the Entice blend.

In Experiments 4 and 5 using the T-tube bioassay apparatus (see EXAMPLE 2; Takács et al. 2013), the inventors tested the response of male mice (Experiment 4) and female mice (Experiment 5) to Feedstims #1 plus Entice (0.001%) against Provoke® Mouse Attractant. The inventors recorded the animals' first choice of aquarium, the time spent in each aquarium, and the test stimulus they fed on first.

In Experiments 4 and 5, male and female mice respectively fed first significantly more often on Feedstims #1 plus Entice than on Provoke® Mouse Attractant (FIG. 3). While Feedstims #1 induced approximately double the feeding response to that provided by Provoke® Mouse Attractant (FIG. 2), adding the attractive composition Entice to Feedstims #1 resulted in mice almost invariably choosing the new composition of Feedstims #1 plus Entice and ignoring Provoke® Mouse Attractant (FIG. 3).

These results suggest that Feedstims #1 plus Entice could be effective as a trap bait in field settings for mice according to some embodiments.

Example #5

Comparative Efficacy of Feedstims #2 Plus Entice Versus Provoke® Mouse Attractant as Trap Baits in a Field Experiment Because of minor problems with consistency of the formulation, gelatin was replaced by agar after the completion of Experiment 5. The new formulation was given the name Feedstims #2. Based on the strong feeding preference of male and female mice for Feedstims #1 plus Entice over Provoke® Mouse Attractant in laboratory Experiments 4 and 5 (FIG. 3), Experiment 6 was designed to compare catches in snap traps baited with the same two baits in the field. Experiment 6 was set up in a potato storage shed on a farm in Delta, British Columbia, Canada from 31 Aug. to 3 Sep. 2012. Twenty-two replicates of paired snap traps were deployed around the accessible interior perimeter of the shed. In each pair, traps were spaced 0.5-1 m apart and about 10 cm away from the wall, with the bait randomly assigned within each pair of traps.

Figure 4:
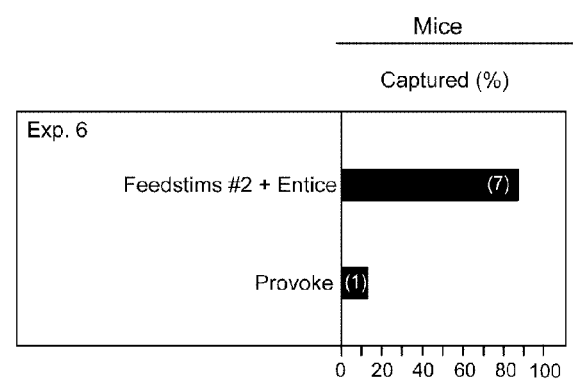
FIG. 4 illustrates the percent of mice captured in Experiment 6 in paired traps (44 replicates), baited with Feedstims #1 (gelatin, water, oat flour, rice flour, wheat bran, fructose, soy lecithin, safflower oil) plus Entice (2-hydroxy-3-methylcyclopent-2-en-1-one; butyric acid; 2,3-butadione; 3-methylbutanal; 6-methyl-(E)-2-hepten-4-one; and γ-octalactone) or baited with a control bait (Provoke® Mouse Attractant) in a potato storage shed from 31 Aug. to 3 Sep. 2012.

In Experiment 6, seven mice were captured in traps baited with Feedstims #2 plus Entice and one mouse was captured in a trap baited with Provoke® Mouse Attractant (FIG. 4). This latter mouse was captured during the set-up of the experiment and possibly blundered into the trap baited with Provoke® Mouse Attractant after being alarmed by the researchers.

The results of Experiment 6 indicate that Feedstims #2 plus Entice is a suitable candidate for developing a highly effective operational mouse bait according to some embodiments.

Example #6

Effect of Carrageenan Gum Powder on Feedstims #2

The results of Experiment 6 showed that a composition comprised of Feedstims #2 plus Entice should suffice as the basis for development of an operational bait for mice. On the other hand, rats are harder to capture in traps. They are wary of anything new placed in their environment (i.e. they are neophobic) and more selective than mice in their choice of food. Thus it was hypothesized that a stronger stimulus would be required to optimize catches of rats in traps than was provided by Feedstims #2 plus Entice. The step-wise development of such a stimulus is described in EXAMPLES 7-11. However, the reluctance of rats to respond rapidly to a baited trap newly placed in their environment often resulted in baits drying out and shrinking to the extent that when rats finally approached they could often remove the bait from a trap without triggering it. One solution to this problem would be to add a humectant that retained water in the bait and retarded drying and shrinking. Carrageenan gum powder was proposed as a humectant that could be used in this case. It was not known if it would affect the feeding response of Norway rats.

In Experiment 7 the present inventors tested Feedstims #2 alone or with carrageenan gum powder (Genugel® carrageenan type CI-102, CP Kelco U.S. Inc., Chicago, Ill.). This new composition was given the name Feedstims #3. The agar, carrageenan gum powder and calcium proprionate mixture was made up in boiling hot water, and mixed immediately with the other ingredients. This prevented premature cooling and solidification of the composition, and had the effect of cooking the cereal components. The experiment was run in the large arena with female rats (see EXAMPLE 3), with the following responses recorded: bait first sniffed (rats approached within 2 cm), bait fed on first, and bait fed on the most.

Figure 5:
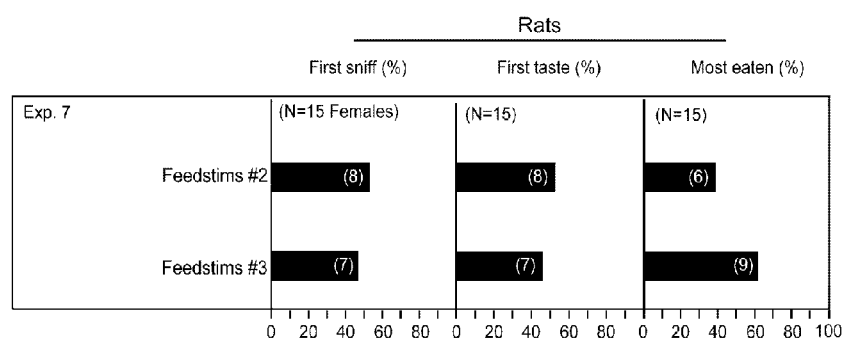
FIG. 5 compares the response in Experiment 7 of female Norway rats, *Rattus norvegicus*, in a large-arena to Feedstims #2 (agar, water, oat flour, rice flour, wheat bran, fructose, soy lecithin, and safflower oil) or Feedstims #3 (Feedstims #2 plus carrageenan gum powder). Data were analyzed by Chi-square test with Yates' correction for continuity. In each of the three sets of paired bars, there was no significant preference (P>0.05) for either test stimulus.

In Experiment 7, female rats responded equally to Feedstims #2 and Feedstims #3 with respect to all three response criteria (first sniff, first taste and most eaten) (FIG. 5). Therefore, it was concluded that carrageenan gum powder can be used as a humectant in Feedstims #3 without inhibiting response to the attractants and feeding stimulants embodied therein.

Example #7

Effect on Rats of Adding Entice to Feedstims #3

Experiments 8 and 9 tested the response of male and female rats to Feedstims #3 plus Entice versus Provoke® Rat Attractant. The experiments were run in the large arena (see EXAMPLE 3), with the following responses recorded: bait first sniffed (rats approached within 2 cm), bait fed on first, and bait fed on the most.

Figure 6:
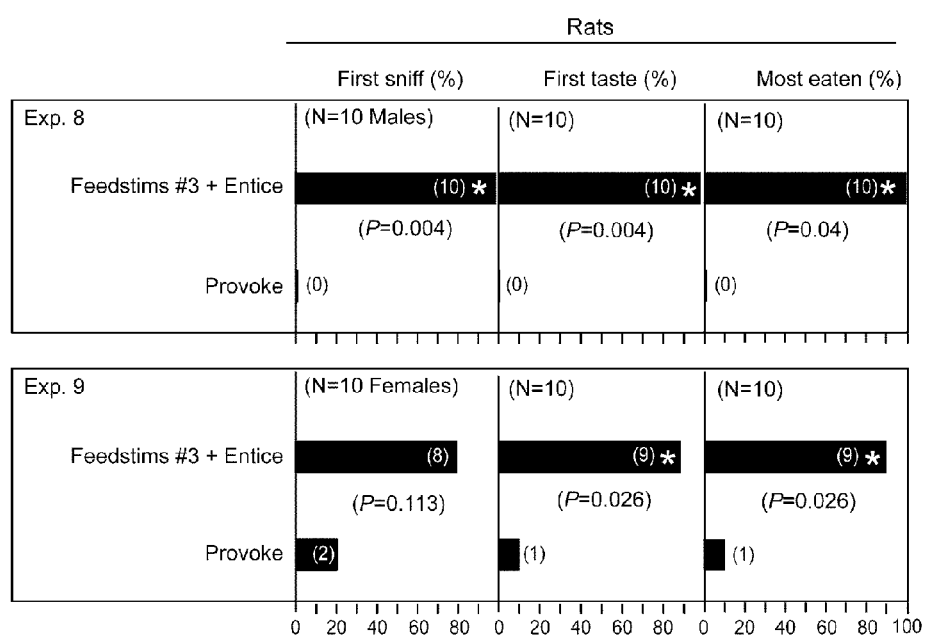
FIG. 6 illustrates the percent of male and female Norway rats, *Rattus norvegicus*, that in large-arena Experiments 8 and 9, sniffed first, tasted first, and consumed more treatment bait [Feedstims #3 (agar, water, oat flour, rice flour, wheat bran, fructose, soy lecithin, safflower oil, and carrageenan gum powder) plus Entice (2-hydroxy-3-methylcyclopent-2-en-1-one; butyric acid; 2,3-butadione; 3-methylbutanal; 6-methyl-(E)-2-hepten-4-one; and γ-octalactone)] or a control bait (Provoke® Rat Attractant). Data in each set of paired bars were analyzed by Chi-square tests with Yates' correction for continuity. In each of the six sets of paired bars, bars with an asterisk (*) indicate a significant preference (P<0.05) for the treatment stimulus.

In Experiment 8, male rats significantly more often sniffed first, tasted first, and consumed more Feedstims #3 plus Entice than Provoke® Rat Attractant (FIG. 6). In Experiment 9, female rats more often sniffed first, significantly more often tasted first, and significantly consumed more Feedstims #3 plus Entice than Provoke® Rat Attractant (FIG. 6). While Feedstims #1 induced less than a two-fold greater feeding response than that provided by Provoke® Rat Attractant (FIG. 2), adding Entice to Feedstims #3 unexpectedly resulted in at least a four-fold better response by male rats than to Provoke® Rat Attractant, and a complete avoidance of Provoke® Rat Attractant by female rats (FIG. 6).

These results indicate that the six attractive chemical components comprising Entice (2-hydroxy-3-methylcyclopent-2-en-1-one; butyric acid; 2,3-butadione; 3-methylbutanal; 6-methyl-(E)-2-hepten-4-one; γ-octalactone) are important constituents of a food bait for rats in some embodiments.

Example #8

Effect of Fish Odor on the Efficacy of Feedstims #3

The present inventors explored whether the addition of fish odor would enhance the efficacy of Feedstims #3. The present inventors produced a new composition (Feedstims #4) in which safflower oil was replaced with cod liver oil (Rexall Brand Corp., Mississauga, Ontario, Canada L4Z 1R9), and another new composition (Feedstims #5), in which safflower oil was replaced with salmon oil (GoldSeal, Canadian Fishing Company, Vancouver, British Columbia, Canada V6A 2Y7)

Experiment 10 then compared the response of female rats to Feedstims #3 and Feedstims #4, and Experiment 11 compared the response of male rats to Feedstims #3 and Feedstims #5. Both experiments were run in the large arena (see EXAMPLE 3), with the following responses recorded: bait first sniffed (rats approached within 2 cm), bait fed on first, and bait fed on the most.

Figure 7:
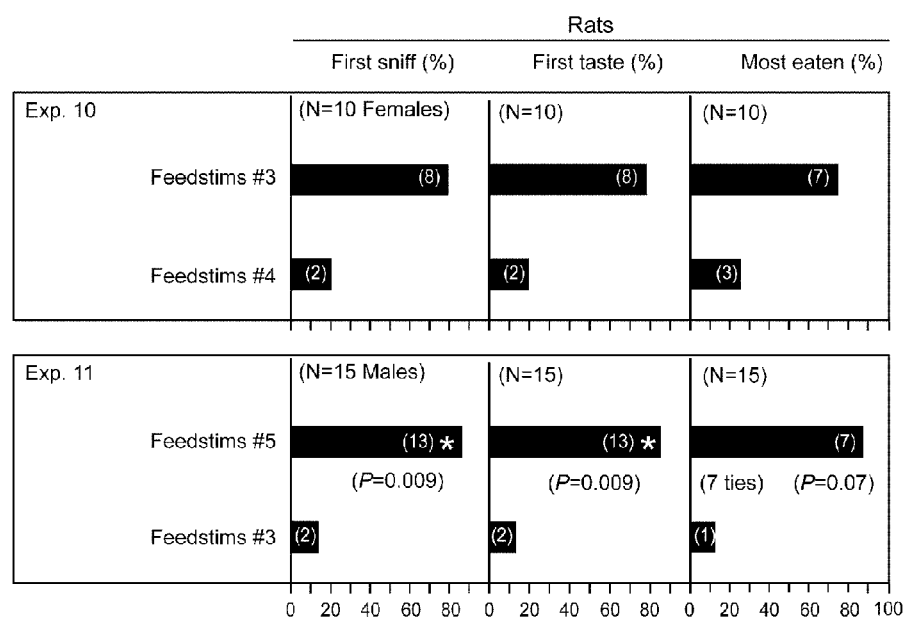
FIG. 7 illustrates the percent of female and male Norway rats, *Rattus norvegicus*, that in large-arena Experiments 10 and 11 sniffed first, tasted first and consumed more Feedstims #3 than Feedstims #4 (Experiment 10) or more Feedstims #5 than Feedstims #3 (Experiment 11). Feedstims #3 consisted of agar, water, oat flour, wheat bran, fructose, soy lecithin, carageenan gum powder and safflower oil. Feedstims #4 was identical to Feedstims #3 except that the safflower oil was replaced with cod liver oil and Feedstims #5 was identical to Feedstims #3 except that safflower oil was replaced with wild salmon oil. Data in each set of paired bars were analyzed by Chi-square tests with Yates' correction for continuity. In each of the six sets of paired bars, bars with an asterisk (*) indicate a significant preference (P<0.05) for the particular stimulus.

In Experiment 10, female rats more often sniffed first, tasted first and consumed more Feedstims #3 than Feedstims #4 (FIG. 7). In Experiment 11, male rats significantly more often sniffed first, significantly more often tasted first, and consumed more Feedstims #5 than Feedstims #3 (FIG. 7).

These results indicate that Norway rats are very selective in their response to fish odor. Cod liver oil in Feedstims #4 inhibited the response to Feedstims #3 by 57%, while wild salmon oil in Feedstims #5 enhanced the response to Feedstims #3 approximately seven-fold.

These results lead to the conclusion that salmon oil can be an important constituent of an operational food bait for rats in some embodiments.

Example #9

Effect of Dimethyltrisulphide and Entice on Feedstims #5

Recently deceased rats (as well as other animals) are often fed on by other rats, implying that the scent of a new carcass is attractive to rats. Blow flies are also attracted to a fresh carcass, suggesting that blow flies and rats may respond to the same semiochemicals. The present inventors have identified dimethyltrisulphide (DMTS) as a predominant semiochemical that attracts blowflies to a fresh rat carcass. The present inventors therefore explored whether DMTS together with the blend of six semiochemicals in Entice could enhance the already very strong response of rats to Feedstims #5 (FIG. 7).

Experiments 12 and 13 tested the response of female and male rats, respectively, to Feedstims #5 plus Entice plus DMTS versus Feedstims #5 alone. Both experiments were run in the large arena (see EXAMPLE 3), with the following responses recorded: bait first sniffed (rats approached within 2 cm), bait fed on first, and bait fed on the most.

Figure 8:
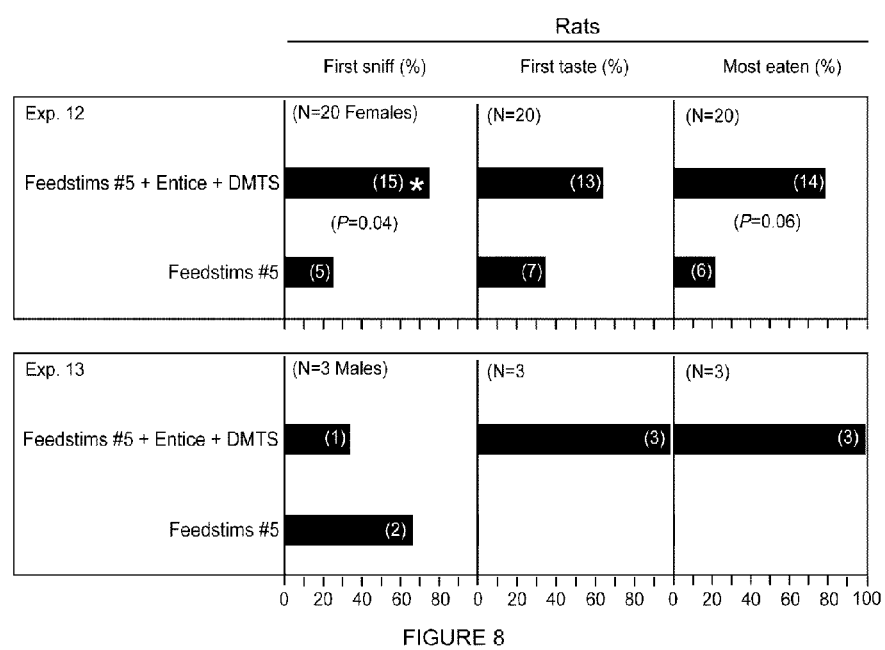
FIG. 8 illustrates the percent of female and male Norway rats, *Rattus norvegicus*, that in large-arena Experiments 12 and 13 sniffed first, tasted first, and consumed more of the treatment bait [Feedstims #5 (agar, water, oat flour, wheat bran, fructose, soy lecithin, carrageenan gum powder, and wild salmon oil) plus Entice (2-hydroxy-3-methylcyclopent-2-en-1-one; butyric acid; 2,3-butadione; 3-methylbutanal; 6-methyl-(E)-2-hepten-4-one; and γ-octalactone) plus dimethyltrisulphide (DMTS)] than the control bait (Feedstims #5). Data in each set of paired bars were analyzed by Chi-square tests with Yates' correction for continuity. In each of the six sets of paired bars, bars with an asterisk (*) indicate a significant preference (P<0.05) for the treatment stimulus.

In Experiment 12, female rats significantly more often sniffed first, more often tasted first, and consumed more Feedstims #5 plus Entice plus DMTS than Feedstims #5 alone (FIG. 8). In Experiment 13, male rats tasted first and consumed more Feedstims #5 plus Entice plus DMTS than Feedstims #5 alone (FIG. 8).

These results clearly indicate that Entice plus DMTS enhanced the response of rats to Feedstims #5, but do not distinguish between the separate effects of Entice and DMTS.

Example 10

Demonstration that Both DMTS and Entice Contribute to Enhanced Efficacy of Feedstims #5

Addition of DMTS and Entice together enhanced the response of rats to Feedstims #5 (FIG. 8) but the relative contribution of DMTS or Entice to the enhanced effect was not clear. Experiments 14-17 were designed to isolate the effect of Entice or DMTS. Specifically, Experiments 14 and 15 tested the response of female and male rats to Feedstims #5 plus DMTS versus Feedstims #5 plus DMTS plus Entice. In turn, Experiments 16 and 17 tested the response of female and male rats to Feedstims #5 plus Entice versus Feedstims #5 plus Entice plus DMTS. The four experiments were run in the large arena (see EXAMPLE 3), with the following responses recorded: bait first sniffed (rats approached within 2 cm), bait fed on first, and bait fed on the most.

Figure 9:
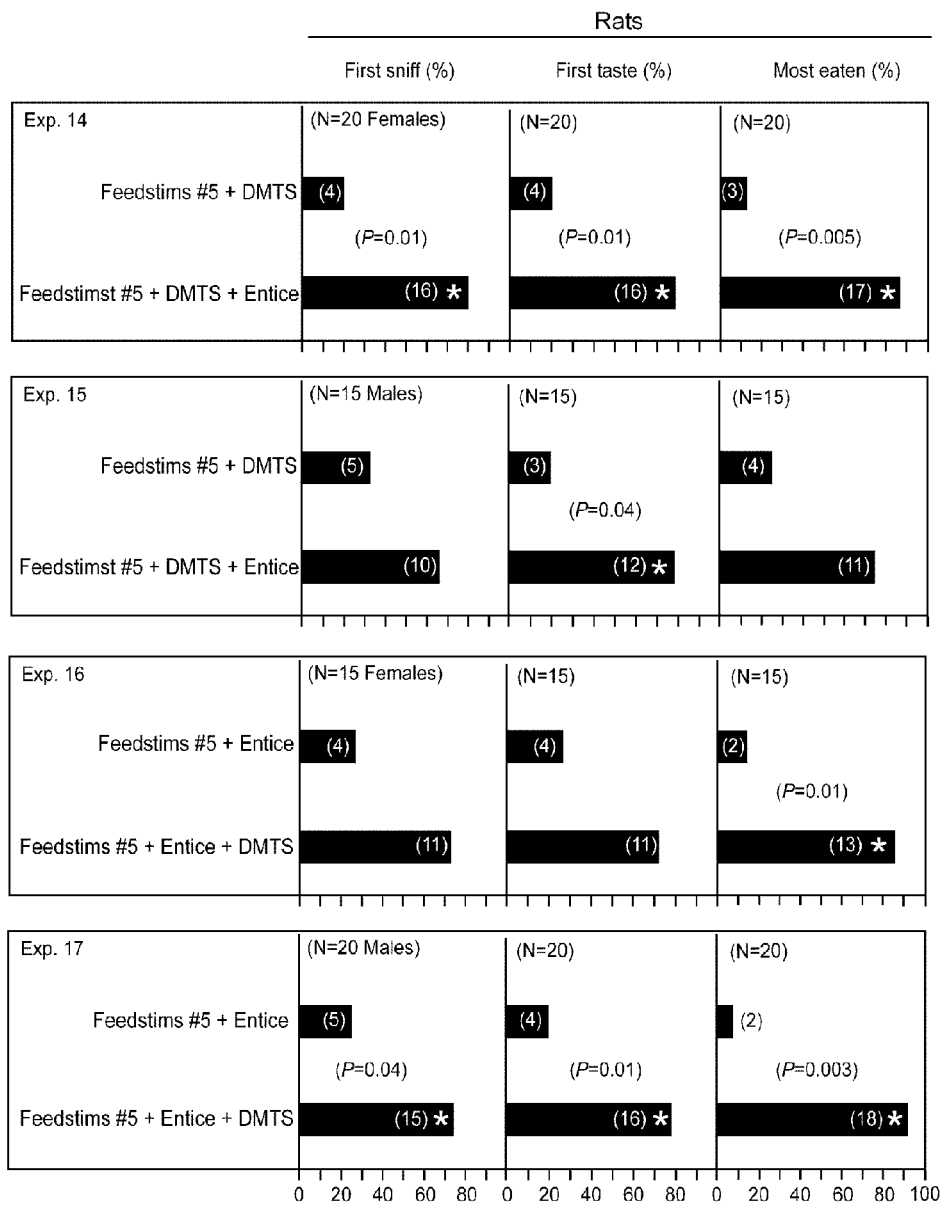
FIG. 9 illustrates the percent of female and male Norway rats (*Rattus norvegicus*) that in large-arena Experiments 14-17 sniffed first, tasted first, and consumed more treatment bait [Feedstims #5 (agar, water, oat flour, wheat bran, fructose, soy lecithin, carrageenan gum powder, and wild salmon oil) plus Entice (2-hydroxy-3-methylcyclopent-2-en-1-one; butyric acid; 2,3-butadione; 3-methylbutanal; 6-methyl-(E)-2-hepten-4-one; and γ-octalactone) plus dimethyltrisulphide (DMTS)] or control bait (Experiment 14, 15: Feedstims #5 plus DMTS; Experiment 16, 17: Feedstims #5 plus Entice). Data in each set of paired bars were analyzed by Chi-square tests with Yates' correction for continuity. In each of the 12 sets of paired bars, bars with an asterisk (*) indicate a significant preference (P<0.05) for the treatment stimulus.

In Experiment 14, female rats significantly more often sniffed first, significantly more often tasted first, and significantly consumed more Feedstims #5 plus DMTS plus Entice than Feedstims #5 plus DMTS (FIG. 9). In Experiment 15, male rats more often sniffed first, significantly more often tasted first, and consumed more Feedstims #5 plus DMTS plus Entice than Feedstims #5 plus DMTS (FIG. 9).

In Experiment 16 female rats more often sniffed first, more often tasted first, and significantly consumed more Feedstims #5 plus Entice plus DMTS than Feedstims #5 plus Entice (FIG. 9). In Experiment 17, male rats significantly more often sniffed first, significantly more often tasted first, and significantly consumed more Feedstims #5 plus Entice plus DMTS than Feedstims #5 plus Entice (FIG. 9).

The results of Experiments 14-17 (FIG. 9) clearly indicate that DMTS and Entice make separate and additive contributions to the efficacy of Feedstims #5. Thus both can be important components of an operational rat bait according to some embodiments.

Example 11

Field Experiment Demonstrating the Superiority of Feedstims #5 Plus Entice Plus DMTS Over Provoke® Rat Attractant With convincing evidence that the inventors had developed a rat bait that was highly effective in the laboratory (FIGS. 7-9), Experiment 18 was set up in a storage shed of a potato farm in Delta, BC, Canada on 22 Oct. 2012. Three replicates of paired snap traps were deployed around the accessible interior perimeter of the shed, and one pair was deployed in a recessed drainage channel. In each pair, traps were spaced 0.5-1 m apart and, if possible, placed 10 cm from walls, with one of two baits randomly assigned within each pair of traps. One bait consisted of Feedstims #5 plus Entice plus DMTS and the other bait was Provoke® Rat Attractant. Every 2-3 days, trap captures were recorded, traps were re-baited and their position within replicates re-randomized.

Figure 10:
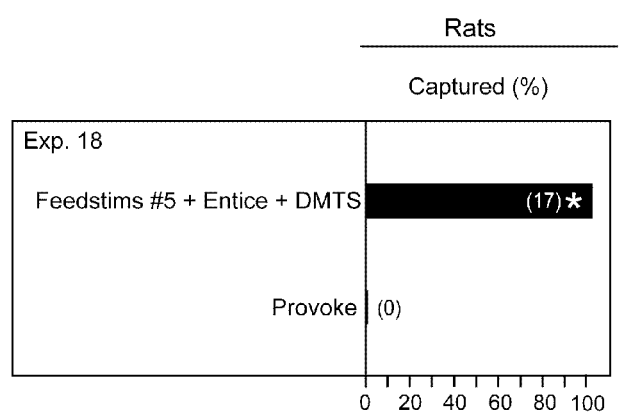
FIG. 10 illustrates the percent of rats, *Rattus norvegicus*, that in field Experiment 18 were captured in snap traps baited with the treatment bait [Feedstims #5 (agar, water, oat flour, wheat bran, fructose, soy lecithin, carrageenan gum powder, and wild salmon oil) plus Entice (2-hydroxy-3-methylcyclopent-2-en-1-one; butyric acid; 2,3-butadione; 3-methylbutanal; 6-methyl-(E)-2-hepten-4-one; and γ-octalactone) plus dimethyltrisulphide (DMTS)] or the control bait [Provoke® Rat Attractant]. Trap catch data were analyzed by a Chi-square test with Yates' correction for continuity. The asterisk (*) indicates a statistically significant preference (P<0.05) for the treatment bait.

In Experiment 18 between 22 October and 4 December, traps baited with Feedstims #5 plus Entice plus DMTS surprisingly captured 17 Norway rats whereas traps baited with Provoke® Rat Attractant captured none (FIG. 10). Unexpectedly, traps baited with Feedstims #5 plus Entice plus DMTS also captured black (roof) rats (*Rattus rattus*), field voles (*Microtus agrestis*) and deer mice (*Peromyscus maniculatus*).

The results of Experiment 18 clearly indicate that the bait consisting of Feedstims #5 plus Entice plus DMTS is much more effective in the field in attracting and capturing Norway rats and other rodents than Provoke® Rat Attractant, which is currently the industry standard. Captures of two species in the genus *Rattus* strongly suggests that all species in this genus will be attracted to and will be induced to feed on Feedstims #5.

As will be apparent to those skilled in the art in the light of the foregoing disclosure, many alterations and modifications are possible in the practice of this invention without departing from the spirit or scope thereof.

This application is intended to cover any variations, uses, or adaptations of the invention using its general principles. Further, this application is intended to cover such departures from the present disclosure as come within known or customary practice in the art to which this invention pertains and which fall within the limits of the appended claims. Accordingly, the scope of the claims should not be limited by the preferred embodiments set forth in the description, but should be given the broadest interpretation consistent with the description as a whole.

REFERENCES

Takács, S. J., R. Gries and G. Gries. 2013. Composition and methods for attracting and stimulating feeding by mice and rats. PCT Patent Application Publication No. WO 2013/003946.

What is claimed is:
1. A composition comprising:
 (i) a cereal-based component;
 (ii) at least one volatile attractive chemical selected from 2-hydroxy-3-methylcyclopent-2-en-1-one, butyric acid, 2,3-butadione, 3-methylbutanal, 5-methyl-(E)-2-hepten-4-one, γ-octalactone, 4-hydroxy-2,5-dimethylfuran-3-one, 5-methyl-4-heptanone, nonanoic acid, decanoic (capric) acid, dodecanoic (lauric) acid, tetradecanoic (myristic) acid, hexadecanoic (palmitic) acid, (Z)-octadec-9-enoic (oleic) acid, octadecanoic (stearic) acid, lactic acid and glycerol; and
 (iii) salmon oil and dimethyltrisulfide.
2. The composition of claim 1 further comprising: a gelling agent, a sugar, an oil, and an emulsifier.
3. The composition of claim 1, wherein the cereal-based component is selected from agar, water, oat flour, rice flour, wheat bran, fructose, soy lecithin, safflower oil, a humectant, and a preservative.
4. The composition of claim 1 comprising at least two of the volatile attractive chemicals.
5. The composition of claim 1, wherein the volatile attractive chemicals are 2-hydroxy-3-methylcyclopent-2-en-1-one, butyric acid, 2,3-butadione, 3-methylbutanal, 5-methyl-(E)-2-hepten-4-one, and γ-octalactone.
6. The composition of claim 1, wherein the volatile attractive chemicals are 2-hydroxy-3-methylcyclopent-2-en-1-one, 2,3-butadione, 3-methylbutanal, 5-methyl-(E)-2-hepten-4-one, 5-methyl-4-heptanone, and γ-octalactone.
7. The composition of claim 1, wherein the cereal-based component comprises cereal flour and cereal bran, and wherein the composition further comprises a humectant.
8. The composition of claim 7, wherein the volatile attractive chemicals are 2 hydroxy-3-methylcyclopent-2-en-1-one, butyric acid, 2,3-butadione, 3-methylbutanal, 5-methyl-(E)-2-hepten-4-one, and γ-octalactone.
9. The composition of claim 7, wherein the volatile attractive chemicals are 2 hydroxy-3-methylcyclopent-2-en-1-one, 2,3-butadione, 3-methylbutanal, 5-methyl-(E)-2-hepten-4-one, 5-methyl-4-heptanone, and γ-octalactone.
10. The composition of claim 1, wherein the cereal-based component comprises oat flour, rice flour, and wheat bran, and wherein the composition further comprises fructose, soy lecithin, gelatin, and a preservative.

11. The composition of claim 10, wherein the volatile active chemicals are 2-hydroxy-3-methylcyclopent-2-en-1-one, butyric acid, 2,3-butadione, 3-methylbutanal, 5-methyl-(E)-2-hepten-4-one, and γ-octalactone.

12. The composition of claim 10, wherein the volatile active chemicals are 2-hydroxy-3-methylcyclopent-2-en-1-one, butyric acid, 2,3-butadione, 3-methylbutanal, 5-methyl-(E)-2-hepten-4-one, 5-methyl-4-heptanone, and γ-octalactone.

13. A composition comprising:
   (i) a cereal-based component, wherein the cereal-based component comprises oat flour, rice flour, and wheat bran;
   (ii) at least one volatile attractive chemical selected from 2-hydroxy-3-methylcyclopent-2-en-1-one, butyric acid, 2,3-butadione, 3-methylbutanal, 5-methyl-(E)-2-hepten-4-one, γ-octalactone, 4-hydroxy-2,5-dimethylfuran-3-one, 5-methyl-4-heptanone, nonanoic acid, decanoic (capric) acid, dodecanoic (lauric) acid, tetradecanoic (myristic) acid, hexadecanoic (palmitic) acid, (Z)-octadec-9-enoic (oleic) acid, octadecanoic (stearic) acid, lactic acid and glycerol; and
   (iii) fructose, soy lecithin, salmon oil, gelatin, a preservative, and dimethyltrisulfide.

14. A method of inducing feeding by mice or rats, the method comprising providing the composition of claim 1 to a mouse or a rat.

15. The method of claim 14, wherein the composition is placed in or near a trap.

16. The method of claim 14, wherein the mouse is from the species *Mus musculus* or the rat is from the species *Rattus norvegicus, Rattus rattus, Rattus annandalei, Rattus enganus, Rattus everetti, Rattus exulans, Rattus hainaldi, Rattus hoogerwerfi, Rattus korinchi, Rattus macleari, Rattus montanus, Rattus morotaiensis, Rattus nativitatis, Rattus ranjiniae, Rattus sanila, Rattus stoicus, Rattus timorensis, Rattus nitidus, Rattus pyctoris, Rattus turkestanicus, Rattus adustus, Rattus andamanensis, Rattus argentiventer, Rattus baluensis, Rattus blangorum, Rattus burrus, Rattus hoffmanni, Rattus koopmani, Rattus losea, Rattus lugens, Rattus mindorensis, Rattus mollicomulus, Rattus osgoodi, Rattus palmarum, Rattus rattus, Rattus satarae, Rattus simalurensis, Rattus tanezumi, Rattus tawitawiensis, Rattus tiomanicus, Rattus bontanus, Rattus foramineus, Rattus marmosurus, Rattus pelurus, Rattus salocco, Rattus xanthurus, Rattus arfakiensis, Rattus arrogans, Rattus elaphinus, Rattus feliceus, Rattus giluwensis, Rattus jobiensis, Rattus leucopus, Rattus mordax, Rattus niobe, Rattus novae guineae, Rattus omichlodes, Rattus pococki, Rattus praetor, Rattus richardsoni, Rattus steini, Rattus vandeuseni, Rattus verecundus, Rattus colletti, Rattus fuscipes, Rattus lutreolus, Rattus sordidus, Rattus tunneyi,* or *Rattus villosissimus*.

17. A method of attracting and inducing feeding by mice and rats, comprising: (a) heat treating the composition of claim 7; and (b) placing the heat treated composition of step (a) in or near a mouse or rat trap.

18. The method of claim 17 wherein step (a) comprises mixing components of the composition with boiling hot water.

19. The method of claim 17, further comprising: (c) combining the heat treated composition with a rodenticide.

20. The method of claim 17, further comprising trapping a mouse or rat.

21. The method according to claim 20, wherein the mouse is from the species *Mus musculus* or the rat is from the species *Rattus norvegicus, Rattus rattus, Rattus annandalei, Rattus enganus, Rattus everetti, Rattus exulans, Rattus hainaldi, Rattus hoogerwerfi, Rattus korinchi, Rattus macleari, Rattus montanus, Rattus morotaiensis, Rattus nativitatis, Rattus ranjiniae, Rattus sanila, Rattus stoicus, Rattus timorensis, Rattus nitidus, Rattus pyctoris, Rattus turkestanicus, Rattus adustus, Rattus andamanensis, Rattus argentiventer, Rattus baluensis, Rattus blangorum, Rattus burrus, Rattus hoffmanni, Rattus koopmani, Rattus losea, Rattus lugens, Rattus mindorensis, Rattus mollicomulus, Rattus osgoodi, Rattus palmarum, Rattus rattus, Rattus satarae, Rattus simalurensis, Rattus tanezumi, Rattus tawitawiensis, Rattus tiomanicus, Rattus bontanus, Rattus foramineus, Rattus marmosurus, Rattus pelurus, Rattus salocco, Rattus xanthurus, Rattus arfakiensis, Rattus arrogans, Rattus elaphinus, Rattus feliceus, Rattus giluwensis, Rattus jobiensis, Rattus leucopus, Rattus mordax, Rattus niobe, Rattus novae guineae, Rattus omichlodes, Rattus pococki, Rattus praetor, Rattus richardsoni, Rattus steini, Rattus vandeuseni, Rattus verecundus, Rattus colletti, Rattus fuscipes, Rattus lutreolus, Rattus sordidus, Rattus tunneyi,* or *Rattus villosissimus*.

* * * * *